United States Patent
Peterson et al.

(10) Patent No.: US 12,065,351 B2
(45) Date of Patent: Aug. 20, 2024

(54) CLEANING MODES IN WATER DISPENSER

(71) Applicant: Quench USA, Inc., King of Prussia, PA (US)

(72) Inventors: Todd Chamberlain Peterson, Haverford, PA (US); Andrew Troy Nuttall, Queen Creek, AZ (US); Theodore Hertz, Lower Gwynedd, PA (US)

(73) Assignee: QUENCH USA, INC., King of Prussia, PA (US)

( * ) Notice: Subject to any disclaimer, the term of this patent is extended or adjusted under 35 U.S.C. 154(b) by 0 days.

(21) Appl. No.: 18/131,721

(22) Filed: Apr. 6, 2023

(65) Prior Publication Data

US 2023/0322541 A1    Oct. 12, 2023

Related U.S. Application Data

(60) Provisional application No. 63/328,366, filed on Apr. 7, 2022.

(51) Int. Cl.
*B67D 1/07* (2006.01)
*A61L 2/18* (2006.01)
(Continued)

(52) U.S. Cl.
CPC ............... *B67D 1/07* (2013.01); *A61L 2/183* (2013.01); *A61L 2/24* (2013.01); *B67D 1/0014* (2013.01);
(Continued)

(58) Field of Classification Search
CPC ...... B67D 1/07; B67D 1/0014; B67D 1/1202; B67D 1/1247; B67D 2001/075;
(Continued)

(56) References Cited

U.S. PATENT DOCUMENTS 5,329,950 A * 7/1994 Barinas ................. B67D 1/07
134/102.1
5,586,439 A * 12/1996 Schlosser ................. F25C 5/10
62/78

(Continued)

FOREIGN PATENT DOCUMENTS

CN     201911943    8/2011
CN     204447778    7/2015
(Continued)

OTHER PUBLICATIONS

International Search Report and Written Opinion issued Oct. 18, 2023 in International Application No. PCT/US2023/017718.

*Primary Examiner* — Regina M Yoo
(74) *Attorney, Agent, or Firm* — Panitch Schwarze Belisario & Nadel LLP

(57) ABSTRACT

A water-dispensing device includes a cold water tank and a fill valve. The tank is in selective fluid communication with a water intake via the fill valve. The device further includes a cold dispensing valve, a spigot in selective fluid communication with the tank via the cold dispensing valve, an ozone generator in fluid communication with the tank, and a drip tray positioned beneath the spigot. The drip tray is in fluid communication with a drain via a drain hose. A controller is configured to perform a cleaning operation by: (i) activating the ozone generator to ozonate water stored in the tank, (ii) opening the cold dispensing valve to empty the tank by dispensing the ozonated water from the tank through the spigot and into the drip tray, and (iii) upon determining the tank is empty, opening the fill valve to refill the tank.

7 Claims, 7 Drawing Sheets

(51) Int. Cl.
  *A61L 2/24* (2006.01)
  *B67D 1/00* (2006.01)
  *B67D 1/12* (2006.01)
(52) U.S. Cl.
  CPC ......... *B67D 1/1202* (2013.01); *B67D 1/1247* (2013.01); *A61L 2202/11* (2013.01); *A61L 2202/14* (2013.01); *B67D 2001/075* (2013.01)
(58) Field of Classification Search
  CPC ........ A61L 2/183; A61L 2/24; A61L 2202/11; A61L 2202/14
  See application file for complete search history.

(56) References Cited

U.S. PATENT DOCUMENTS

| | | | | |
|---|---|---|---|---|
| 6,334,328 | B1* | 1/2002 | Brill | A23G 9/325 62/347 |
| 9,480,762 | B2 | 11/2016 | Wang et al. | |
| 9,750,835 | B2 | 9/2017 | Wang et al. | |
| 9,803,907 | B2* | 10/2017 | Erbs | F25C 1/12 |
| 11,382,994 | B2* | 7/2022 | Almblad | A61L 2/183 |
| 2003/0094422 | A1* | 5/2003 | Perkins | A61L 2/183 210/764 |
| 2004/0245281 | A1* | 12/2004 | Oke | B67D 1/07 222/1 |
| 2013/0272923 | A1 | 10/2013 | Wang et al. | |
| 2015/0068983 | A1 | 3/2015 | Pawlow | |
| 2016/0009537 | A1* | 1/2016 | Orita | B67D 1/0857 222/144.5 |
| 2016/0016776 | A1* | 1/2016 | Orita | B67D 1/0009 222/146.1 |
| 2016/0016777 | A1* | 1/2016 | Orita | B67D 1/001 222/54 |
| 2016/0031694 | A1* | 2/2016 | Orita | B67D 1/0861 222/638 |
| 2016/0046508 | A1* | 2/2016 | Orita | B67D 1/07 222/146.1 |
| 2016/0362285 | A1 | 12/2016 | Yui et al. | |
| 2018/0207305 | A1* | 7/2018 | Almblad | F25C 5/182 |
| 2020/0361758 | A1 | 11/2020 | Fantappié et al. | |
| 2022/0023472 | A1* | 1/2022 | Claussner | A61L 2/26 |

FOREIGN PATENT DOCUMENTS

| | | | |
|---|---|---|---|
| CN | 213850125 | 8/2021 | |
| WO | WO-2013128665 A1 * | 9/2013 | ........... B67D 1/0004 |
| WO | 2018074417 A1 | 4/2018 | |

* cited by examiner

| General setup | User view settings | Cleaning settings | Prep/refurb setting |

Daily ozone cycle
- Run time — 5 min
- Air purge time — 5 min
- Run frequency interval — 8 hrs
- At dispense ozone cycle — 0 sec Ozone status screen visible?

IMPORTANT: the following cycles will automatically purge the cold tank and dispense up to 3 gallons of water. The drip tray must be connected to a drain or drip tray will overflow and water damage will occur.
  I confirm drip tray is connected to a drain Deep clean cycle   CAUTION: WILL DISPENSE WATER
- Timing of    Date   21-5-27
- first cycle  Time   4 :00
- Frequency  Every  6  Weeks
- Ozone run time   10 Minutes Auto-circulation freshness cycle                    CAUTION: WILL DISPENSE WATER OFF
  ○ Run if system is unused for          48 Hours
  ⦿ Run every                             1 Days
    Specify time to run                   22 :00
    Water dispense run time              30 Seconds  SET Connected

Fig. 5

CLEANING MODES IN WATER DISPENSER

CROSS-REFERENCE TO RELATED APPLICATIONS

This application claims the benefit of U.S. Provisional Patent Application No. 63/328,366, filed on Apr. 7, 2022, entitled "Cleaning Modes for Water Dispenser", the entire contents of which are incorporated by reference herein.

BACKGROUND

Embodiments described herein relate generally to water dispensers, and more particularly, to modes for cleaning and maintaining a water dispenser.

Water dispensers should be cleaned periodically to maintain fresh and sanitary drinking water. Such cleanings should involve all of the plumbing and components with which the water or other relevant materials may come into contact. This can include storage tanks, tubing, valves, and even the drip tray. One way in which cleaning may be performed is to inject ozone into the water, thereby making the water a sanitizing solution. In some devices, the ozonated water is introduced to the cold water storage tank, but typically only feed small amounts of water through any associated tubing, and completely ignore the drip tray because a user is instructed to place a vessel beneath the dispensing valve to catch small amounts of dispensed, ozonated water. The ozonated water then typically remains in the storage tank, where it may await consumption by a user.

Water dispensers and their filtration system can also be susceptible to performance hindrance when water is not dispensed on a fairly regular basis. Stagnation of water in the tank and in the filters can lead to increases in total dissolved solids (TDS) or bacteria growth, which can harm the water dispenser and cause performance to decline.

It is desirable to provide a water dispenser that is capable of thorough cleaning of all of the plumbing that may come into contact with the drinking water, including the drip tray. It is further desirable to provide a water dispenser capable of cycling water during periods of non-use to keep the water that is in the filters and storage tank from becoming stagnant. It is also desirable that these processes are capable of being performed at times when users will not be present so as not to delay water consumption during the cleaning cycle.

BRIEF SUMMARY

Briefly stated, one embodiment comprises a water-dispensing device including a cold water tank configured to store water at a temperature below 50° F. and a fill valve. The cold water tank is in selective fluid communication with a water intake via the fill valve. The water-dispensing device further includes a cold dispensing valve, a spigot in selective fluid communication with the cold water tank via the cold dispensing valve, an ozone generator in fluid communication with the cold water tank, and a drip tray positioned beneath the spigot. The drip tray is in fluid communication with a drain via a drain hose. A controller is configured to perform a cleaning operation by: (i) activating the ozone generator to ozonate water stored in the cold water tank, (ii) opening the cold dispensing valve to empty the cold water tank by dispensing the ozonated water from the cold water tank through the spigot and into the drip tray, and (iii) upon determining the cold water tank is empty, opening the fill valve to refill the cold water tank.

In one aspect, the controller is further configured to deactivate the ozone generator in response to a determination that an ozonation condition of the water in the cold water tank is reached. In another aspect, the controller is further configured to operate a timer for ozonation and deactivate the ozone generator in response to expiration of the timer.

In yet another aspect, the controller is further configured to be in wireless communication with and receive a schedule for the cleaning operation from an external device.

In still another aspect, the water-dispensing device further includes an air pump and an air stone. The air stone is configured to be submerged within the water in the cold water tank and in fluid communication with the ozone generator via the air pump.

In yet another aspect, the controller is further configured to, in response to a determination of a malfunction at the drip tray, close the cold dispensing valve and output an error.

Another embodiment comprises a method for cleaning a water-dispensing device having a cold water tank, a fill valve for placing the cold water tank in selective communication with a water intake, a cold dispensing valve, a spigot in selective fluid communication with the cold water tank via the cold dispensing valve, an ozone generator, a drip tray positioned beneath the spigot and in fluid communication with a drain via a drain hose, and a controller. The method includes activating, by the controller, the ozone generator to ozonate water in the cold water tank, opening, by the controller, the cold dispensing valve to empty the cold water tank by dispensing the ozonated water from the cold water tank through the spigot and into the drip tray, and upon determining that the cold water tank is empty, opening, by the controller, the fill valve to refill the cold water tank.

In one aspect, the method further includes deactivating, by the controller, the ozone generator in response to a determination that an ozonation condition of the water in the cold water tank is reached. In another aspect, the controller operates a timer for ozonation and deactivates the ozone generator in response to expiration of the timer. In yet another aspect, opening of the cold dispensing valve occurs generally simultaneously with or after deactivation of the ozone generator.

In still another aspect, the controller operates a timer for emptying the cold water tank and determines the cold water tank is empty upon expiration of the timer.

In yet another aspect, the controller activates the ozone generator at a predetermined time.

In still another aspect, the controller, in response to a determination of a malfunction at the drip tray, closes the cold dispensing valve and outputs an error.

Yet another embodiment comprises a method for performing a fresh water cycling in a water-dispensing device having one or more water tanks, one or more fill valves for placing the one or more water tanks in selective communication with a water intake, one or more dispensing valves, a spigot in selective fluid communication with the one or more water tanks via one of the one or more dispensing valves, a drip tray positioned beneath the spigot and in fluid communication with a drain via a drain hose, and a controller. The method includes determining, by the controller, that a designated time for fresh water cycling for a designated one of the one or more water tanks has been reached, in response to determining that the designated time has been reached, opening, by the controller, one of the one or more dispense valves to dispense water from the designated one of the one or more water tanks through the spigot and into the drip tray, upon determining that a preset cycle condition has been reached, closing, by the controller, the one of the one or more dispense valves, and opening, by the controller, one of the one or more fill valves to refill the designated one of the one or more water tanks.

In one aspect, the preset cycle condition is a preset period of time.

In another aspect, the preset cycle condition is removal of a predetermined amount of water from the designated one of the one or more water tanks.

In yet another aspect, the opening of the one of the one or more fill valves occurs generally simultaneously with or after the closing of the one of the one or more dispense valves.

In still another aspect, the one or more water tanks includes a cold water tank and a hot water tank.

BRIEF DESCRIPTION OF THE SEVERAL VIEWS OF THE DRAWINGS

The following detailed description of preferred embodiments will be better understood when read in conjunction with the appended drawings. For the purpose of illustration, there are shown in the drawings embodiments which are presently preferred. It should be understood, however, that the invention is not limited to the precise arrangements and instrumentalities shown.

In the drawings:

FIG. 5 is a screenshot of an example application that can be used in an external device to control and/or monitor operation of a water-dispensing device in accordance with the present invention;

DETAILED DESCRIPTION

Figure 1:
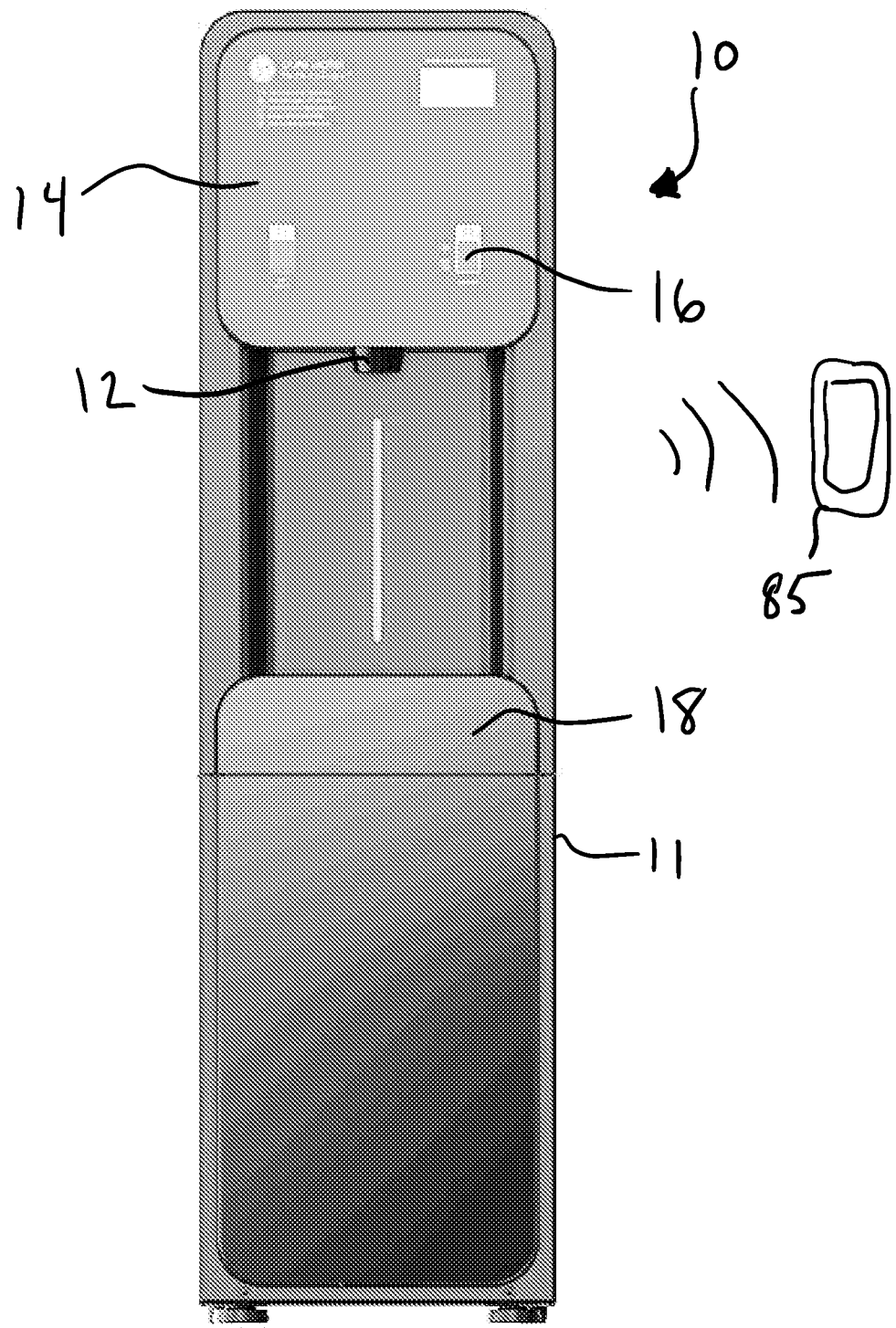
FIG. 1 is a front side elevational view of a water-dispensing device in accordance with a first example embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an", as used in the claims and in the corresponding portions of the specification, mean "at least one."

It should also be understood that the terms "about," "approximately," "generally," "substantially" and like terms, used herein when referring to a dimension or characteristic of a component, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to FIG. 1, there is shown a first example embodiment of a water-dispensing device 10 in accordance with the present invention. FIG. 1 depicts a free-standing water-dispensing device 10, but the water-dispensing device 10 may be of any conventional type in keeping within the spirit and scope of the invention, such as a countertop dispenser, a built-in (e.g., cabinet-mounted) dispenser, or the like. The water-dispensing device 10 may have a spigot 12 for dispensing water into a vessel (not shown), such as a cup, glass, or the like. The dispensing device 10 may further include an operation panel 14, which can provide a dispensing actuator 16, such as a button, touchscreen icon, or the like. In the embodiment of FIG. 1, the dispensing actuator 16 is a touch-free sensor for hygienic operation. For example, a user need only bring a finger or hand in proximity to the sensor 16 to initiate a water dispensing operation. A drip tray 18 may be positioned beneath the spigot 12. The drip tray 18 may support the vessel during a water dispensing operation, but is preferably also configured to provide a container to catch water accidentally spilled from the vessel or the spigot 12, or, as explained in further detail below, for receiving water during cleaning or cycling operations.

Figure 2:
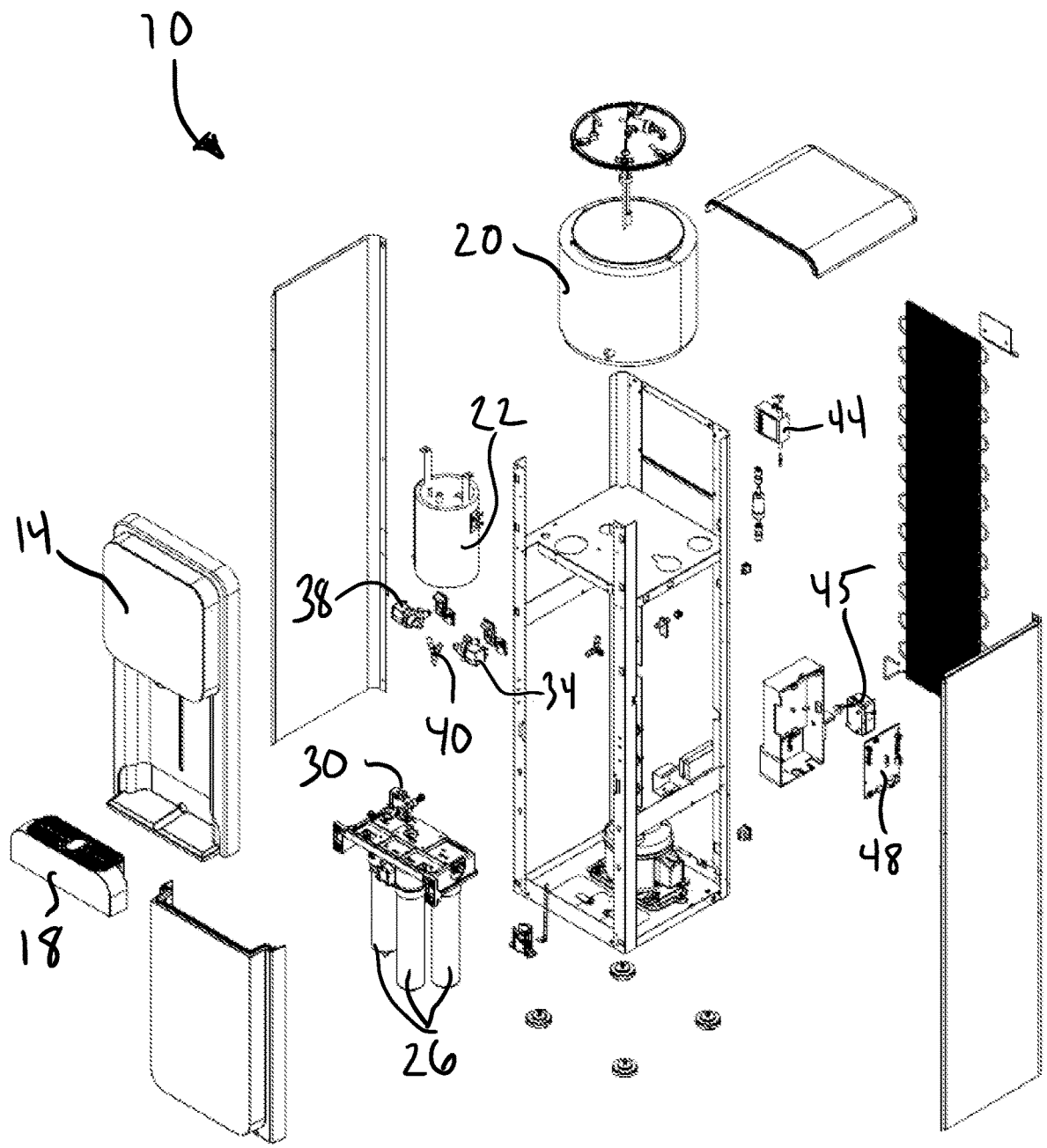
FIG. 2 is a perspective, exploded view of the water-dispensing device of FIG. 1.
Figure 3:
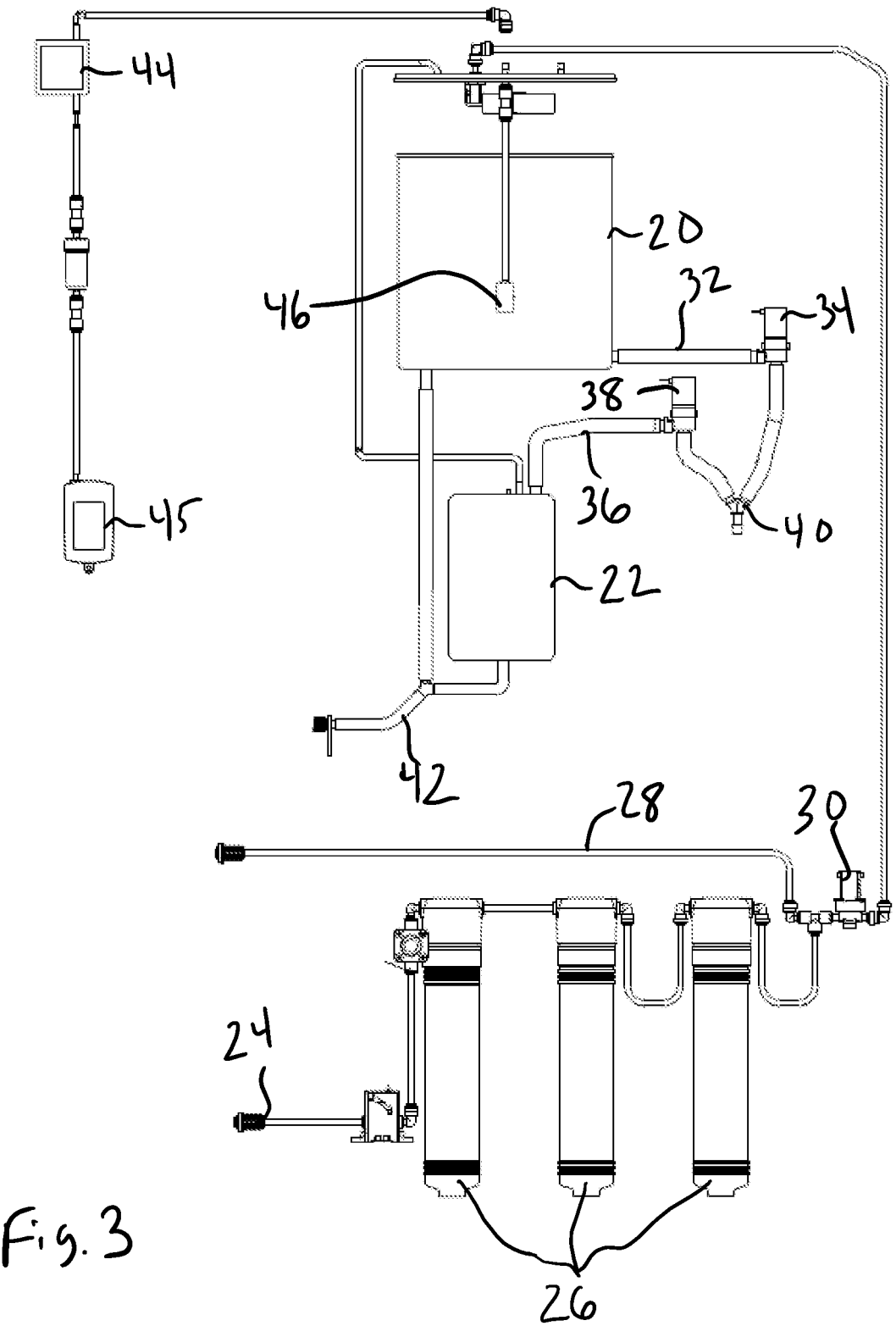
FIG. 3 is a schematic plumbing diagram of the water-dispensing device of FIG. 1.

Referring to FIGS. 2-3, the water-dispensing device 10 may include a cold water tank that is preferably configured to store water at a temperature below 50° F. The cold water tank may be insulated and include equipment (not shown) for chilling water contained therein, as is conventionally known. The cold water tank 20 shown in FIGS. 2-3 may be capable of storing up to three gallons of cold water, although other volumes may be used as well. The water-dispensing device 10 may additionally or alternatively include a hot water tank 22 that is preferably configured to store water at a temperature over 160° F. The hot water tank 22 may be insulated and include equipment (not shown) for heating water contained therein, as is conventionally known. The hot water tank 22 shown in FIGS. 2-3 may be capable of storing up to half of a gallon of hot water, although other volumes may be used as well.

The water-dispensing device 10 may include a water intake 24 that may be directly or indirectly connected to a water source (not shown), such as a building water supply, a container, or any other like source of water. One or more filters 26 may be located upstream of the cold and hot water tanks 20, 22 in order to filter water before it is conditioned (e.g., heated or cooled) and stored. For example, the filters 26 may be sediment, carbon, reverse osmosis, ultra filtration, and/or other like types of filters. After the incoming water is filtered, there may be an auxiliary line 28 that allows the filtered water to proceed to other external water-use devices, such as a coffee maker, an ice maker, or the like. However, the filtered water is preferably mainly used to fill the cold and/or hot water tanks 20, 22. One or more fill valves 30 may be disposed between the filters 26 (and/or the water intake 24) and the cold and/or hot water tanks 20, 22 to control filling operations. The fill valve 30 may be a solenoid valve or other type of electrically-actuated valve.

The cold water tank 20 may be in fluid communication with a cold water dispensing line 32 that can be controlled by a cold dispensing valve 34, which may be a solenoid valve or other type of electrically-actuated valve. Similarly, the hot water tank 22 may be in fluid communication with a hot water dispensing line 36 that can be controlled by a hot dispensing valve 38, which may be a solenoid valve or other type of electrically-actuated valve. As the example in FIG. 1 shows a single spigot 12, the cold and hot dispensing valves 34, 38 may lead to a common dispensing wye 40. However, in some embodiments, separate spigots may be provided for dispensing cold and hot water. The cold and hot water tanks 20, 22 may each also connect to a drain line 42 in the event either tank needs to be emptied.

To sanitize the cold water tank 20, the water-dispensing device 10 may further include an ozone generator 44. An air pump 45 may be used to move the ozone produced by the ozone generator 44 into the cold water tank 20. While the air pump 45 is shown separately from the ozone generator 44 in the drawings, the ozone generator 44 may have an air pump incorporated therewith. An air stone 46 in fluid communication with the ozone generator 44 may be submerged within the water in the cold water tank 20 to distribute the ozone. While an ozone generator 44 is shown in the present example for sanitizing the cold water tank 20, other conventional sanitization methods may be used as well, such as ultraviolet sanitization or colloidal silver sanitization, or the like.

For the hot water tank 22, the ozone generator 44 or a separate ozone generator (not shown) may be used if desired, but the high temperatures (preferably over 160° F.) of the hot water may provide sufficient sanitation of the hot water tank 22 and associated waterways for ordinary use.

Various operations and processes of the water-dispensing device 10, for example, manipulation of the fill valve 30, the cold and hot dispensing valves 34, 38, and/or other valves, operating heating or chilling elements (not shown), actuating the ozone generator 44, and/or the like, may be performed by at least one controller 48, which may by a microcontroller unit (MCU), a central processing unit (CPU), a microprocessor, an application specific controller (ASIC), a programmable logic array (PLA), combinations thereof, or the like. The controller 48 may include or be coupled to a memory (not shown) that may store code or software for carrying out processes described herein and/or carrying out other operations of the water-dispensing device 10 and may store any captured data for later transfer to remote or external devices. It should be further appreciated that although controller 48 is referred to in this example as a single component, the controller 48 may include a plurality of individual devices, with control functions divided among the individual devices. The controller 48 may be wired or wirelessly connected to components of the water-dispensing device 10 necessary for carrying out the operations and processes described herein.

Figure 4:
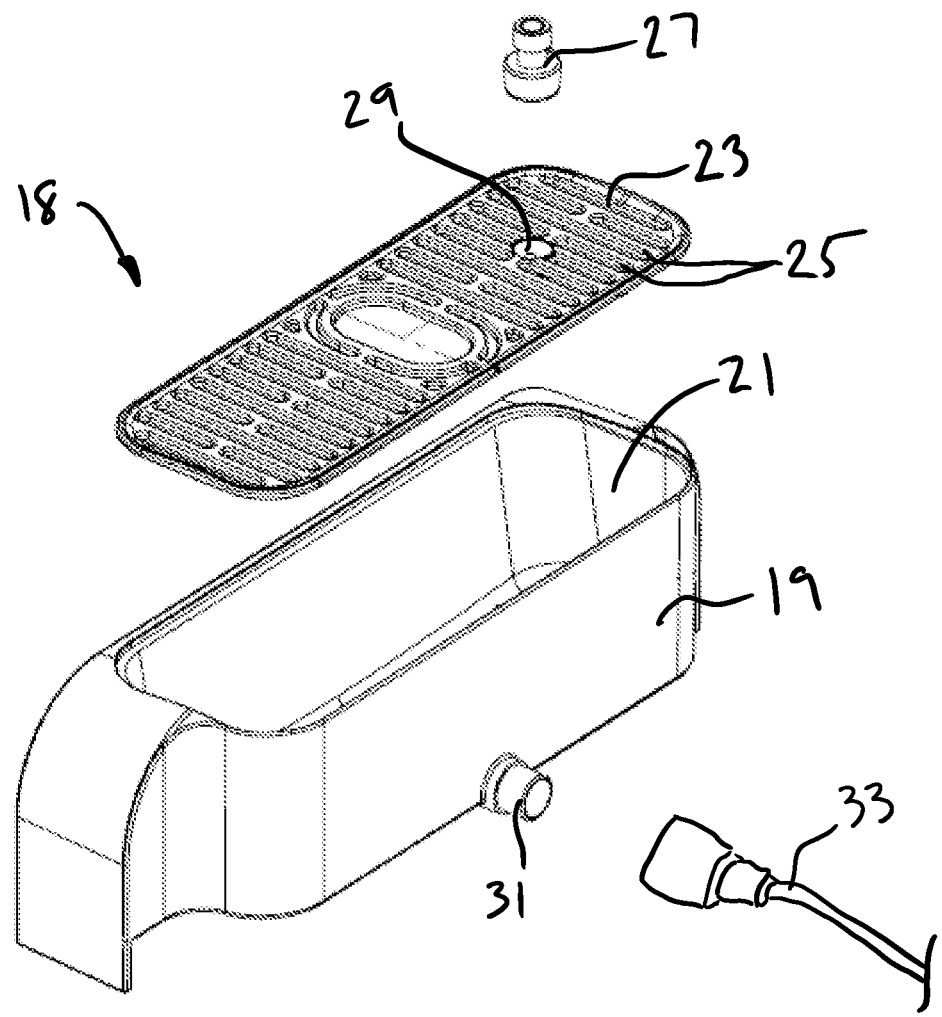
FIG. 4 is a left, rear side, perspective exploded view of the drip tray of the water-dispensing device of FIG. 1.

In particular, the controller 48 may be configured to perform at least a thorough cleaning of the cold water tank 20 and/or a fresh water cycling, as will be described in further detail below. However, in order to perform either of these operations, the drip tray 18 of the water-dispensing device 10 is preferably connected to a drain, sewage line, or the like (not shown) so that the full or other large amount of water in the cold water tank 20 may be emptied through the spigot 12 with minimal spillage. FIG. 4 shows an exploded view of an example drip tray 18. The drip tray 18 may include a body 19 for attachment to a housing 11 (see FIG. 1) of the water-dispensing device 10. The body 19 may define a cavity 21 configured to face the spigot 12 when installed on the water-dispensing device 10. The cavity 21 may be closed by a cover 23 having a plurality of slots or other small openings 25 arranged to allow water to enter the cavity 21 from above. A float 27 may be provided to indicate when water present in the cavity 21 should be emptied. For example, a top end of the float 27 may be level with a top of the cover 23 when the cavity 21 is empty or has a lower level of water retained therein, but as water rises in the cavity 21, the float 27 may be forced upward through a float hole 29 in the cover 23 to provide a visual indication of the increasing water level in the drip tray 18.

The body 19 may include an outlet connection 31 configured to receive a drain hose 33 or similar type of tubing connection. The outlet connection 31 puts the cavity 21 in fluid communication with the drain hose 33 so that water retained in the cavity 21 may be directed out of the drip tray 18 and into a drain (not shown), to which the drain hose 33 may be directly or indirectly connected.

Figure 6:
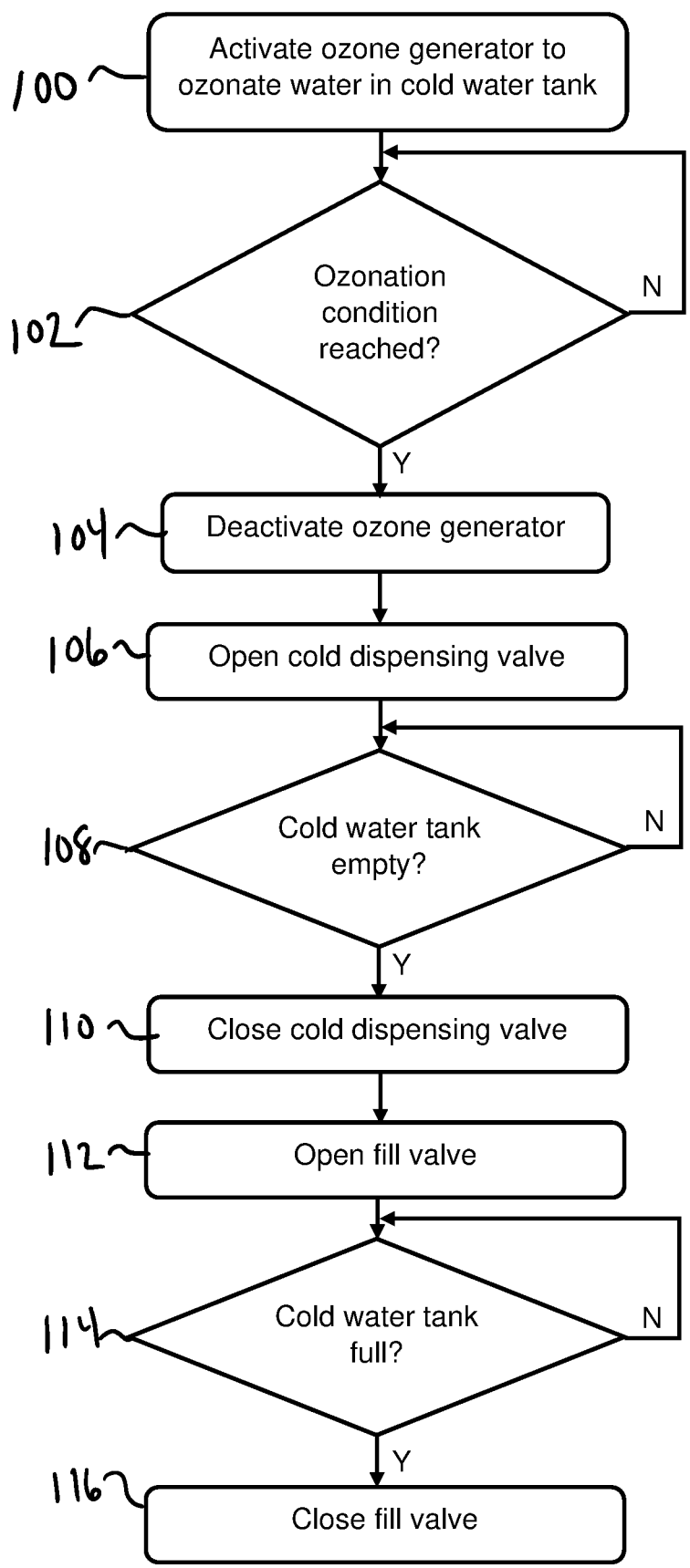
FIG. 6 is a flow chart illustrating an example method performed by a controller for implementing a deep cleaning operation.

FIG. 6 shows an example of a method that may be performed by the controller 48 for implementing a deep cleaning of the cold water tank 20. During deep cleaning, the water-dispensing device 10 would be unable to perform ordinary dispense operations. Accordingly, as will be explained in further detail below, it is preferable that such a cleaning operation be performed during periods of light to no use, such as outside of business hours, overnight, or the like. At step 100, the controller 48 may activate the ozone generator 44 to ozonate the water stored in the cold water tank 20. This may further include activating the air pump 45 and opening any valves (not shown) that might be necessary to let the ozone enter the cold water tank 20. The run time of the ozone generator can be adjusted by a user or operator and can depend on local conditions. For example, in an office, ten (10) minutes of run time for the ozone generator 44 may be sufficient. In a bakery, for example, which may present dusty conditions, twenty (20) minutes may be required. In a hospital, thirty (30) minutes may be desirable. A default setting may be fifteen (15) minutes.

At step 102, the controller 48 determines whether an ozonation condition is reached. For example, in one embodiment, the controller 48 may run the ozone generator 44 for a preset period of time, preferably 20-30 minutes, although other time periods may be used as desired. If the time period has not yet elapsed, the controller 48 may continue to operate the ozone generator 44. In another embodiment, the controller 48 may monitor an ozone level in the cold water tank 20, e.g., using an ozone sensor or the like. Until a preset ozone level is reached, for example, the controller 48 may continue to operate the ozone generator 44. Other conditions may be used as well for determining whether to continue running the ozone generator 44 or not.

Once the ozonation condition is reached, at step 104, the controller 48 may deactivate the ozone generator 44, which may also include switching off the air pump 45 and closing any associated valves. At step 106, the controller 48 may open the cold dispensing valve 34, allowing the ozonated water from the cold water tank 20 to flow through cold water dispensing line 32, the cold dispensing valve 34, the common dispensing wye 40, and out the spigot 12. The cold dispensing valve 34 may be opened generally simultaneously with the deactivation of the ozone generator 44, or a delay between the two steps may also be introduced. The water will then descend into the drip tray 18 where it can be removed via the drain hose 33 to the drain. In this manner, the cold water tank 20 and all paths emanating therefrom to the spigot, as well as the drip tray 18 (which may come into contact with a user's cup or glass during normal dispensing operations) can be sanitized.

In some embodiments, the drip tray 18 may include a sensor (not shown), such as a fill level sensor or the like, to indicate whether there is a problem with draining of the drip tray 18, such as a clog, a disconnected hose 33, or some other malfunction. To avoid overflow in the drip tray 18, the sensor may communicate with the controller 48, which can close the cold dispensing valve 34 in response. In addition, the controller 48 may output an error code or other message to a user or operator, via the control panel 14, an external device 85, or the like, about the malfunction in the drip tray 18. The controller 48 may prevent further dispensing until the drip tray 18 is emptied and the condition cleared.

At step 108, the controller 48 determines whether the cold water tank 20 is empty. In some embodiments, this may be done using one or more water level sensors (not shown), such as float sensors, optical sensors, inductive-type sensors, capacitive-type sensors, combinations thereof, or the like in the cold water tank 20. In other embodiments, the controller 48 may utilize a timer programmed with a known or estimated amount of time for the cold water tank 20 to empty through the spigot 12. Upon determining that the cold water tank 20 is empty, the controller 48 at step 110 may close the cold dispensing valve 34.

Simultaneously or afterward, the controller 48 at step 112 may open the fill valve 30 to allow fresh water from the water source to begin refilling the now sanitized cold water tank 20. At step 114, the controller 48 may monitor whether the cold water tank 20 is full, using, for example, one or more of the fill level sensors described above, a timer, or other like methods for determining a fill state of the cold water tank 20. Upon finding that the cold water tank 20 is full, the controller 48 moves to step 116 where it may close the fill valve 30. The deep cleaning is complete and the water-dispensing device 10 may be used again for dispensing operations.

A similar operation may be performed on the hot water tank 22 if it is determined that ozonation thereof is desirable.

In some embodiments, it may be desirable to avoid draining the cold water tank 20 through the spigot 12 and drip tray 18. To allow as thorough a cleaning as possible in the system, a bypass and associated electrically-actuable valve (not shown) may be located upstream of and generally adjacent to the common dispensing wye 40. The bypass may connect, either directly or indirectly, to the drain. In this way, the ozonated water can still sanitize the cold water tank 20, the cold water dispensing line 32, and the cold dispensing valve 34. In some other embodiments, it may be desirable to simply drain ozonated water directly from the cold water tank 20 via an additional port and associated electrically-actuable valve (not shown) that can connect to the drain. In still further embodiments, one or both of the above-described solutions may be provided as user-selectable alternatives to the spigot 12 and drip tray 18 method described herein, such that the draining method may be appropriately suited to the location and configuration of the water-dispensing device 10. For example, one of these alternatives may be selected if a drain hose 33 is not available to drain from the drip tray 18.

Figure 7:
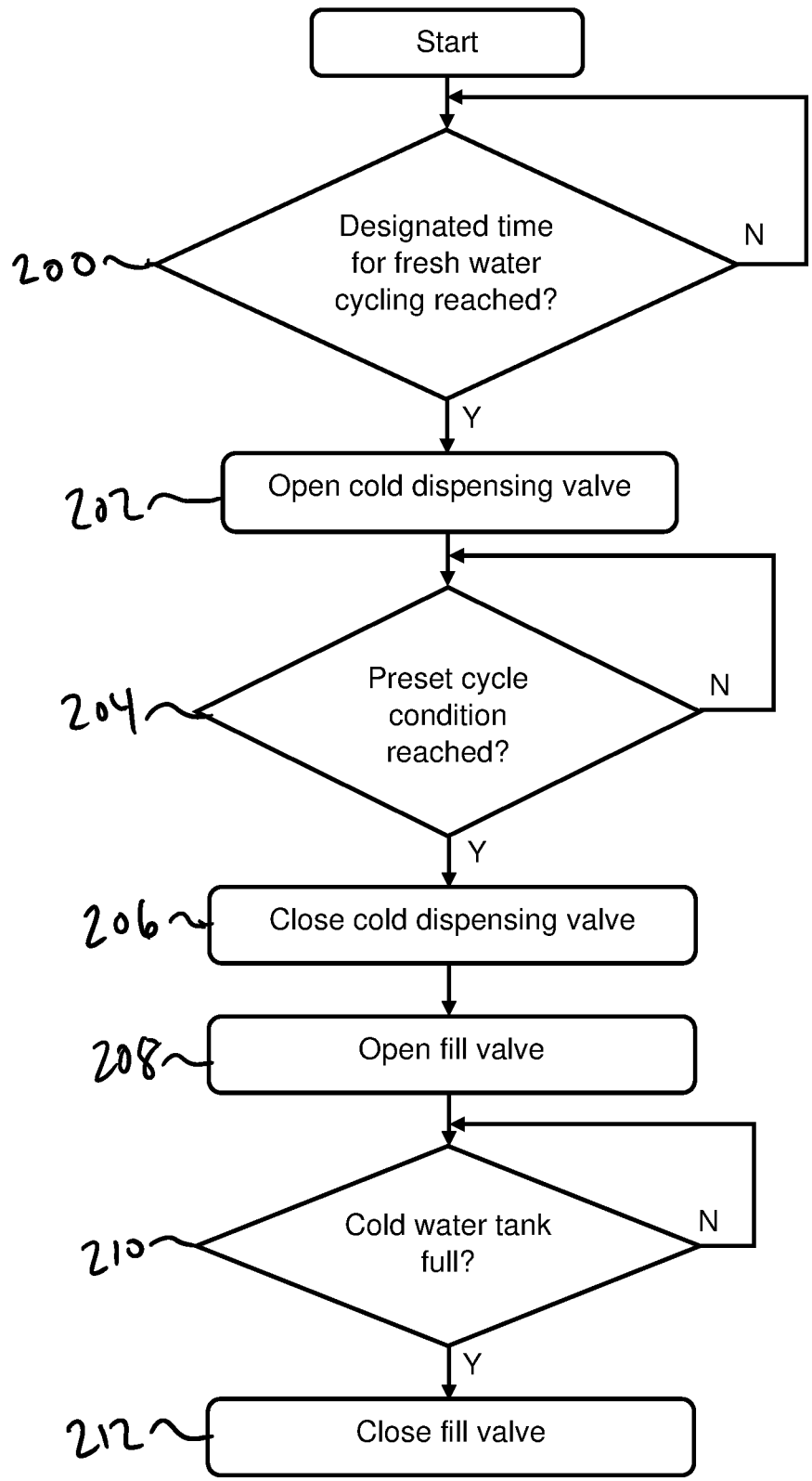
FIG. 7 is a flow chart illustrating an example method performed by a controller for implementing a fresh water cycling operation.

FIG. 7 shows an example of a method that may be performed by the controller 48 for implementing a fresh water cycling operation. At step 200, the controller 48 may determine whether a designated time for fresh water cycling has been reached. For example, the controller 48 may be programmed to perform a cycling operation according to a preset schedule—e.g., once a day, once every three days, once a week, or the like. Alternatively, the controller 48 may be programmed to perform a cycling operation after a programmed period of inactivity. For example, the controller 48 may initiate the cycling operation if 72 hours (or some other time period) have passed since water was last dispensed.

At step 202, the controller 48 may open the cold dispensing valve 34, allowing at least a portion of the water from the cold water tank 20 to flow through cold water dispensing line 32, the cold dispensing valve 34, the common dispensing wye 40, and out the spigot 12. The water will then descend into the drip tray 18 where it can be removed via the drain hose 33 to the drain. At step 204, the controller 48 may determine whether a preset cycle condition has been reached. For example, the controller 48 may be programmed to allow a predetermined amount of water to be removed from the cold water tank 20, which may be determined by one of the fill level sensors described above. The predetermined amount may be all of the water contained in the cold water tank 20 or only a portion thereof. Alternatively, the controller 48 may use a timer and leave the cold dispensing valve 34 open for only a preset period of time (e.g., 30 seconds or the like). Upon reaching the present condition, the controller 48 may, at step 206, close the cold dispensing valve 34.

Simultaneously or afterward, the controller 48 at step 208 may open the fill valve 30 to allow fresh water from the water source to begin refilling the cold water tank 20. At step 210, the controller 48 may monitor whether the cold water tank 20 is full, using, for example, one or more of the fill level sensors described above, a timer, or other like methods for determining a fill state of the cold water tank 20. Upon finding that the cold water tank 20 is full, the controller 48 moves to step 212 where it may close the fill valve 30. The fresh water cycling is complete and the water-dispensing device 10 may be used again for dispensing operations.

A similar operation may be performed on the hot water tank 22 as well, if desired. Such an operation may be performed in conjunction with a cycling in the cold water tank 20, or may be performed independently—e.g., if hot water has not been dispensed in the previous 72 hours but cold water has been periodically dispensed within that same time frame, the controller 48 may perform cycling on the hot water tank 22 only.

Scheduling of the above-described deep cleaning and fresh water cycling operations may be preprogrammed at the controller 48, but in a number of embodiments, a user or operator of the water-dispensing device 10 may have the option to program or adjust a schedule for one or both operations. For example, the operation panel 14, or some other portion on or contained within the housing 11, may provide a keypad, touch panel, or like user interface (not shown) to receive instructions for scheduling various operations of the water-dispensing device 10, such as those described above.

In some embodiments, the water-dispensing device 10, and particularly the controller 48, may be configured for wired communication (e.g., via USB, Ethernet, IEEE 1394, or the like) or wireless communication (e.g., via WI-FI, BLUETOOTH, ZIGBEE, Z-WAVE, 3G, 4G, or 5G cellular, infrared, or the like) with an external device 85, such as a smartphone, laptop, tablet, desktop, or the like. A user may be able to access features and operations of the water-dispensing device 10 through a web browser, a software application installed on the external device 85, or the like.

FIG. 5 is a screenshot 70 of an example application that may be deployed on the external device 85. In this example, the external device 85 connects with the controller 48 via BLUETOOTH and can generally provide information related to a condition and status of the water-dispensing device 10 as well as allow for selection of a number of operation settings. In the example screenshot 70 shown in FIG. 5, a page for selecting cleaning settings 71 is provided.

In this example, the user is requested to confirm 72 that the drip tray 18 is connected to a drain. If confirmation is not provided, options for deep cleaning and/or fresh water cycling may not be selectable or visible. In other embodiments, the water-dispensing device 10 may include one or more sensors (not shown) to automatically confirm the drain connection with the drip tray 18.

An option 73 to enable the deep cleaning operation may be provided. Upon activation, the user may be permitted to select, for example, a first cleaning time 74, a frequency 75 of operation, and a run time 76 for the ozone generator 44. More or fewer parameters may be listed and selectable. In some embodiments, the application may allow an on-demand activation of a deep cleaning operation.

Similarly, an option 77 to enable the fresh water cycling operation may be provided. Upon activation, the user may be permitted to select between an option of running after a period of non-use 78, or an option of running on a periodic basis 79. If the first option 78 is selected, the user may be able to set a desirable non-use time period 80. If the second option 79 is selected, the user may be able to select a repeating time period 81 and/or a specific time of day to run 82. For either option, the user may also be able to select 83 how long to run the water-dispensing device 10 (e.g., 30 seconds) during a fresh water cycling operation. Although two options 78, 79 are presented in the example of FIG. 5, the application may only provide one. In some other embodiments, more or fewer parameters and options may be listed and selectable. In some embodiments, the application may allow an on-demand activation of a fresh water cycling operation.

Those skilled in the art will recognize that boundaries between the above-described operations are merely illustrative. The multiple operations may be combined into a single operation, a single operation may be distributed in additional operations and operations may be executed at least partially overlapping in time. Further, alternative embodiments may include multiple instances of a particular operation, and the order of operations may be altered in various other embodiments.

While specific and distinct embodiments have been shown in the drawings, various individual elements or combinations of elements from the different embodiments may be combined with one another while in keeping with the spirit and scope of the invention. Thus, an individual feature described herein only with respect to one embodiment should not be construed as being incompatible with other embodiments described herein or otherwise encompassed by the invention.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined herein.

We claim:

1. A method for cleaning a water-dispensing device having a cold water tank, a fill valve for placing the cold water tank in selective communication with a water intake, a cold dispensing valve, a spigot in selective fluid communication with the cold water tank via the cold dispensing valve, an ozone generator, a drip tray positioned beneath the spigot and in fluid communication with a drain via a drain hose, and a controller, the method comprising:
   activating, by the controller, the ozone generator to ozonate water in the cold water tank;
   opening, by the controller, the cold dispensing valve to empty the cold water tank by dispensing the ozonated water from the cold water tank through the spigot and into the drip tray; and
   upon determining that the cold water tank is empty, opening, by the controller, the fill valve to refill the cold water tank.

2. The method of claim 1, further comprising deactivating, by the controller, the ozone generator.

3. The method of claim 2, wherein the controller operates a timer for ozonation and deactivates the ozone generator in response to expiration of the timer.

4. The method of claim 2, wherein opening of the cold dispensing valve occurs generally simultaneously with or after deactivation of the ozone generator.

5. The method of claim 1, wherein the controller operates a timer for emptying the cold water tank and determines the cold water tank is empty upon expiration of the timer.

6. The method of claim 1, wherein the controller activates the ozone generator at a predetermined time.

7. The method of claim 1, wherein the controller, in response to a determination of a malfunction at the drip tray, closes the cold dispensing valve and outputs an error.

* * * * *